(12) United States Patent
Leung

(10) Patent No.: US 6,444,858 B2
(45) Date of Patent: *Sep. 3, 2002

(54) METHOD OF REDUCING FLOCK DURING ALKOXYLATION

(75) Inventor: Philip Leung, Webster, TX (US)

(73) Assignee: Baker Hughes Incorporated, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/294,422

(22) Filed: Apr. 19, 1999

(51) Int. Cl.⁷ ............................................. C07C 41/03
(52) U.S. Cl. ........................ 568/579; 568/607; 568/609; 568/611; 568/612; 568/616; 568/618; 568/621; 568/626; 568/630; 568/631; 568/632; 568/642; 568/664; 568/665; 568/667; 568/671; 568/687
(58) Field of Search ................................ 568/618, 607, 568/609, 611, 612, 616, 626, 630, 631, 632, 642, 659, 664, 665, 667, 687, 671, 579, 621

(56) References Cited

U.S. PATENT DOCUMENTS 3,894,093 A * 7/1975 Raizer et al. ........... 260/613 B
4,465,877 A * 8/1984 Edwards ..................... 568/618
4,593,142 A * 6/1986 Yang ........................... 568/618

OTHER PUBLICATIONS

Transportation and Unloading Operations, pp. 1–14, Feb. 2001.*
Lewis, Hawley's Condensed Chemical Dictionary, 12th edition, p. 491, 1993.*
Chemical Backgrounders–Ethylene Oxide, http://www.n-sc.org/ehc.ew/chems/ehtyoxid.htm., Jul. 1997.*
Chemical Bacgrounders–Propylene Oxide, http://www.n-sc.org/ehc.ew/chems/propoxid.htm., Dec. 1998.*
OSHA Fact Sheets, http://www.osha–slc.gov/OshDoc/Fact_data/FSNO95–17.html., Jan. 1995.*

* cited by examiner

Primary Examiner—Rosalynd Keys
(74) Attorney, Agent, or Firm—Paula D. Morris & Associates, PC.

(57) ABSTRACT

The present invention provides a method for alkoxylating organic compounds comprising contacting an organic compound adapted to be alkoxylated with an alkylene oxide in a reaction vessel under conditions effective to alkoxylate the organic compound. The alkylene oxide is maintained in vapor form during transport to said reaction vessel, during discharge into said reaction vessel, and during contacting of the organic compound with the alkylene oxide. The result is an alkoxylated product containing less flocculant.

62 Claims, 1 Drawing Sheet

METHOD OF REDUCING FLOCK DURING ALKOXYLATION

FIELD OF THE INVENTION

Figure 1:
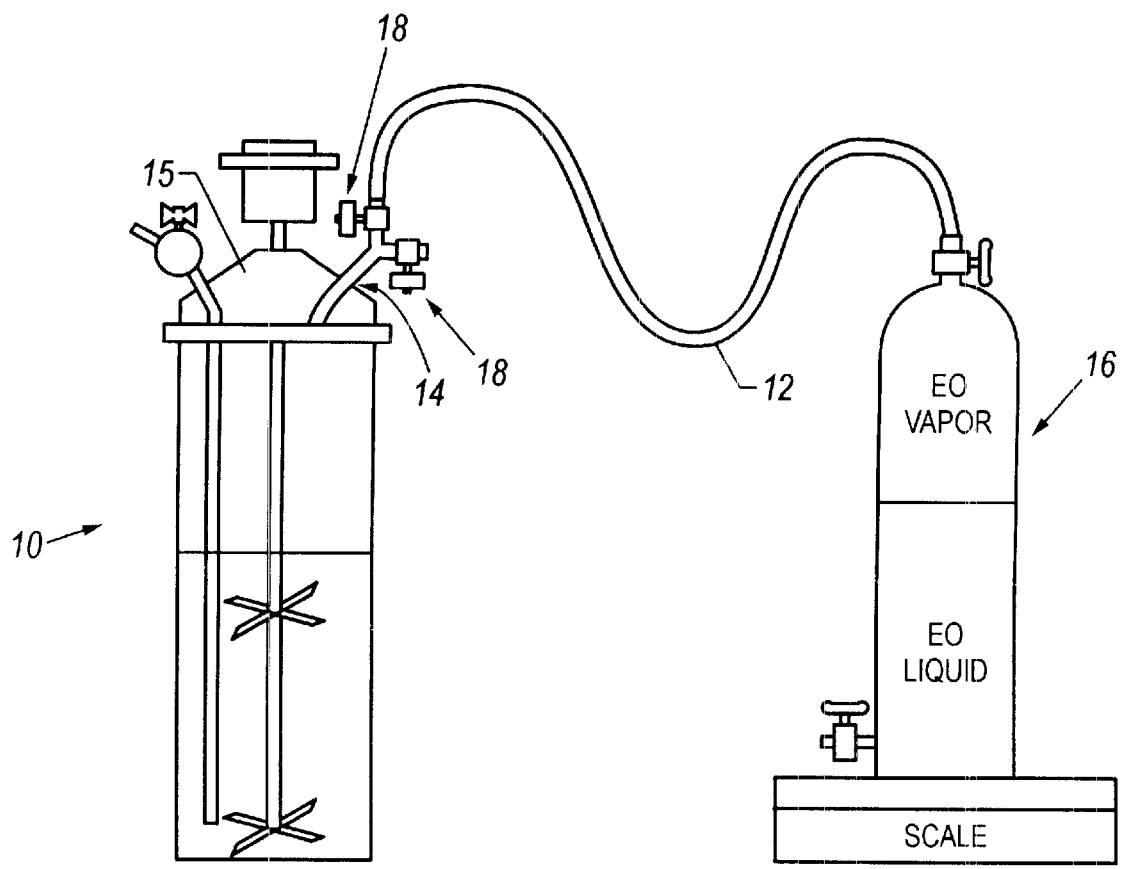

The present invention is a method for alkoxylating organic compounds, preferably polyalkylene glycols, by exposing the organic compounds to alkylene oxide vapor which is not compressed into a liquid phase for purposes of transport or introduction into the reactor. The method results in alkoxylation products containing less, little, or no flock.

BACKGROUND OF THE INVENTION

A variety of organic materials react under suitable conditions with an adducting material, such as an alkylene oxide—particularly ethylene oxide or propylene oxide—to form alkoxylated organic materials. Typically, the alkylene oxide adducting material is compressed into liquid form for transport to and discharge into the reactor. Unfortunately, even if the alkylene oxide is decompressed into the vapor phase before the alkoxylation reaction begins, the previous compression of the alkylene oxide into the liquid phase tends to increase flock in the alkoxylation product. A method is needed by which to form alkoxylated products containing no, little, or less flock.

SUMMARY OF THE INVENTION

The present invention provides a method comprising contacting an organic compound adapted to be alkoxylated with an alkylene oxide in a reaction vessel under conditions effective to alkoxylate the organic compound. The alkylene oxide is maintained in vapor form before and during transport to said reaction vessel, during discharge into the reaction vessel, and during contact with the organic compound.

DETAILED DESCRIPTION OF THE INVENTION

The present invention provides a method for producing an alkoxylation product with no, little, or less flock. According to the present method, the alkylene oxide adducting material is not compressed into liquid form in order to transport and/or to introduce the material into the alkoxylation reactor. The alkylene oxide is both transported and discharged into the reactor in the vapor phase. Without limiting the present invention to any particular theory or mechanism, it is believed that compression of ethylene oxide into the liquid phase produces minute amounts of oligomers or polymers which contribute to the formation of flock in the substrate. The present invention is believed to reduce flock by avoiding the formation of these oligomers or polymers in the alkylene oxide.

The alkoxylation reaction, itself, takes place under standard conditions. The reaction takes place at any suitable temperature, preferably from about 10° C. to about 160° C. For practical purposes, most commercial operations will be carried out in the temperature range of from about 50° C. to about 200° C.

The method is useful to alkoxylate any suitable alkoxylatable organic material. Suitable materials include, but are not necessarily limited to polyhydric, unsaturated, linear or branched alcohols, saturated alcohols, alkyl phenols, polyols, aldehydes, ketones, amines, amides, organic acids, and mercaptans. Preferred organic materials are normally selected from the group consisting of (a) polyhydric alcohols containing a total of from about 2 to about 30 carbon atoms and having the general formula

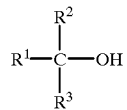

wherein $R^1$, $R^2$, and $R^3$ independently are selected from the group consisting of linear and branched acyclic groups, alicyclic groups, aryl groups, cyclic groups, and hydrogen, and may contain one or more functional groups selected from the group consisting of amine groups, carboxyl groups, hydroxy groups, halogen atoms, nitro-groups, carbonyl groups, and amide groups. Representative but non-exhaustive examples of various polyhydric alcohols which can be alkoxylated according to the present invention are: ethylene glycol, 1,2-propylene glycol 1,4-butanediol; 1,6-hexanediol; 1,10-decanediol; 1,3-butylene glycol; diethylene glycol; diethylene glycol monobutyl ether; diethylene glycol monomethyl ether; diethyl glycol monoethyl ether, dipropylene glycol; dipropylene glycol monomethyl ether ethylene glycol monomethyl ether; ethylene glycol monoethyl ether; ethylene glycol monobutyl ether; hexylene glycol; mannitol, sorbitol; pentaerythritol; dipentaerythritol, tripentaerythritol; trimethylolpropane; trimethylolethane; neopentyl glycol; diethanolamine; triethanolamine; diisopropanolamine; triisopropanolamine; 1,4-dimethylolcyclohexane; 2,2-bis(hydroxymethyl)propionic acid; 1,2-bis(hydroxymethyl)benzene; 4,5-bis(hydroxymethyl) furfural; 4,8-bis(hydroxymethyl)tricyclo-[5,2,1,0] decane; tartaric acid; 2-ethyl-1,3-hexanediol; 2-amino-2-ethyl-1,3-propanediol; triethylene glycol; tetraethylene glycol; glycerol; ascorbic acid. Representative but non-exhaustive examples of various aldehydes and ketones which can be alkoxylated according to the present invention are lauryl aldehyde benzaldehyde; 2-undecanoneacetophenone; 2,4-pentandione; acetylsalicyclic acid; ortho-chlorobenzaldehyde; para-chlorobenzaldehyde; cinnamic aldehyde; diisobutyl ketone; ethylacetoacetate; ethyl amyl ketone; camphor; para-hydroxybenzaldehyde; 2-carboxybenzaldehyde; 4-carboxybenzaldehyde; salicylaldehyde; octyl aldehyde; decyl aldehyde; p-methoxybenzaldehyde; p-aminobenzaldehyde; phenylacetaldehyde; acetoacetic acid; 2,5-dimethoxybenzaldehyde; T-naphthyl aldehyde; terephthaldehyde;

(b) aldehydes and ketones having from about 2 to about 30 carbon atoms and having the general formula

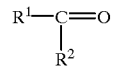

wherein $R^1$ and $R^2$ independently are selected from the group consisting of hydrogen, linear and branched acyclic groups, alicyclic groups, cyclic groups, and aryl groups, and may contain one or more functionalities selected from the group consisting of carboxyl groups, hydroxyl groups, halogen atoms, nitro-groups, amine groups, and amide groups;

(c) primary, secondary and tertiary amides having from about 1 to about 30 carbon atoms and having the general formula

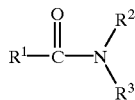

wherein $R^1$, $R^2$, and $R^3$ independently are selected from the group consisting of hydrogen, linear and branched acyclic groups, alicyclic groups, cyclic groups, and aryl groups, and may contain one or more functionalities selected from the group consisting of hydroxyl groups, carboxyl groups, carbonyl groups, amine groups, nitro-groups, and halogen atoms. Representative but non-exhaustive examples of amides which can be alkoxylated according to the instant invention are: formamide; benzamide; acetanilide, salicylamide; acetoacetanilide; ortho-acetoacetotoluidide; acrylamide; N,N-diethyltoluamide; N,N-dimethylacetamide; N,N-dimethylformamide; phthalimide; octylamide; decylamide; laurylamide; stearylamide; N,N-dimethylollaurylamide; N,N-dimethylacrylamide; para-chlorobenzamide; para-methoxybenzamide; para-aminobenzamide; para-hydroxybenzamide; ortho-nitrobenzamide,; N-acetyl-para-aminophenol; 2-chloroacetamide; oxamide; N,N-methylene-bis-acrylamide;

(d) primary, secondary, and tertiary amines having from about 1 to about 30 carbon atoms, and having the general formula

wherein $R^1$, $R^2$, and $R^3$ independently are selected from the group consisting of hydrogen, linear and branched acyclic groups, alicyclic groups, cyclic groups, and aryl groups, and may contain one or more functionalities selected from the group consisting of hydroxyl groups, carbonyl groups, halogen atoms, carboxyl groups, nitro-groups, and amide groups. Representative but non-exhaustive examples of amines which can be alkoxylated according to the present invention are: aniline; benzylamine; hexadecylamine, triphenylamine. aminoacetic acid anthranilic acid, cyclohexylamine, tert-octylamine; ortho-phenylenediamine; meta-phenylenediamine; para-phenylenediamine; N-acetyl-para-aminophenol; 2-amino-4-chlorophenol; 2-amino-2-ethyl-1,3-propanediol; ortho-aminophenol; para-aminophenol; para-aminosalicyclic acid, benzyl-N,N-dimethylamine; tert-butylamine; 2-chloro-4-aminotoluene; 6-chloro-2-aminotoluene; meta-chloroaniline; ortho-chloroaniline; para-chloroaniline; 4-chloro-2-nitroaniline; cyclohexylamine, dibutylamine; 2,5-dichloroaniline; 3,4-dichloroaniline; dicyclohexylamine; diethanolamine; N,N-diethylethanolamine; N,N-diethyl-meta-toluidine; N,N-diethylaniline; diethylenetriamine; diisopropanolamine; N,N-dimethylethanolamine; N,N-dimethylaniline; 2,4-dinitroaniline, diphenylamine, ethyl-para-aminobenzoate; N-ethylethanolamine; N-ethyl-1-naphthylamine; N-ethyl-ortho-toluidine, N-ethylaniline, ethylenediamine; hexamethylenetetraamine, 2,4-lutidine; N-methylaniline; methyl anthranilate; p,p'-diaminodiphenyl methane; ortho-nitroaniline; para-nitroaniline; tert-octylamine; piperazine; ethanolamine; isopropanolamine; ortho-toluidine; para-toluidine; 2,4-toluenediamine; triethanolamine; tributylamine; triisopropanolamine; 2,4-dimethylxylidine; para-methoxyaniline, nitrilotriacetic acid; N-phenyl-1-naphthylamine;

(e) organic acids having from about 1 to about 30 carbon atoms, and having the general formula

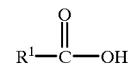

wherein $R^1$ is selected from the group consisting of hydrogen, linear and branched acyclic groups, alicyclic groups, cyclic groups, aryl groups, and may contain one or more functionalities selected from the group consisting of carbonyl groups, hydroxyl groups, halogen atoms, nitro-groups, amine groups, and amide groups. Representative but non-exhaustive examples of organic acids which can be alkoxylated according to the present invention are: formic acid; acetic acid; valeric acid; heptanoic acid; 2-ethylhexanoic acid; lauric acid; stearic acid; oleic acid; tall oil acids hydrogenated tall oil acids; benzoic acid salicyclic acid; adipic acid; azelaic acid; fumaric acid; citric acid; acrylic acid; aminoacetic acid; para-aminosalicyclic acid; anthranilic acid; butyric acid; propionic acid; ricinoleic acid; chloroacetic acid; ortho-chlorobenzoic acid; 2,4-dichlorophenoxyacetic acid; tert-decanoic acid; para-aminobenzoic acid; abietic acid; itaconic acid; lactic acid; glycolic acid; malic acid; maleic acid; cinnamic acid; para-hydroxybenzoic acid; methacrylic acid; oxalic acid; myristic acid; palmitic acid; tert-pentanoic acid; phenylacetic acid; mandelic acid; sebacic acid; tallow fatty acids; hydrogenated tallow fatty acids; tartaric acid; trichloroacetic acid; 2,4,5-trichlorophenoxyacetic acid; undecylenic acid; crotonic acid; pelargonic acid; acetoacetic acid; para-nitrobenzoic acid; ascorbic acid; nitrilotriacetic acid; naphthenic acid; 1-naphthoic acid, trimellitic acid, (f) alkyl phenols having from about 6 to about 30 carbon atoms, and having the general formula

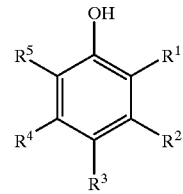

wherein $R^1$, $R^2$, $R^3$, $R^4$, and $R^5$ independently are selected from the group consisting of hydrogen, halogen atoms, hydroxyl groups, nitro-groups, carbonyl groups, linear and branched acyclic groups, alicyclic groups, cyclic groups, aryl groups, and may contain one or more functionalities selected from the group consisting of halogen atoms, ether groups, nitrogroups, carboxyl groups, carbonyl groups, amine groups, amide groups, and hydroxyl groups. Representative but non-exhaustive examples of various phenols which can be alkoxylated according to the present invention are: phenol, ortho-cresol, meta-cresol; para-cresol, 2,4-dimethylphenol 2,5-dimethylphenol; 2,6-dimethylphenol; ortho-chlorophenol; meta-chlorophenol; para-chlorophenol; para-nitrophenol; para-methoxyphenol; salicyclic acid; meta-hydroxyacetophenone; para-aminophenol; ortho-phenylphenol; nonylphenol; octylphenol; t-butyl-para-cresol; hydroquinone; catechol; resorcinol; pyrogallol, 1-naphthol, 2-naphthol; 4,4'-isopropylidenediphenol (bisphenol A); methyl salicylate; benzyl salicylate; 4-chloro-2-nitrophenol; para-t-butylphenol; 2,4-di-t-amylphenol; 2,4-dinitrophenol; para-hydroxybenzoic acid; 8-hydroxyquinoline; methyl para-hydroxybenzoate; 2-nitro-para-cresol; ortho-nitrophenol; para-phenylphenol; phenyl salicylate; salicylaldehyde; p-hydroxy benzaldehyde; 2-amino-4-chlorophenol; ortho-aminophenol; salicylamide;

(g) mercaptans of the general formula

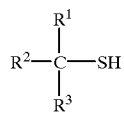

wherein $R^1$, $R^2$ and $R^3$ independently are selected from the group consisting of hydrogen, linear and branched acyclic groups, alicyclic groups, cyclic groups, and aryl groups having from about 1 to about 30 carbon atoms, and may contain one or more functionalities selected from the group consisting of carboxyl groups, hydroxyl groups, halogen atoms, nitro-groups, amine groups, and amide groups, and (h) alcohols having the general formula ROH wherein R is selected from the group consisting of a linear and branched alkyl groups having from about 1 to about 30 carbon atoms, aryl groups, cyclic groups having from about 6 to about 30 carbon atoms, and olefinic and acetylenic groups having from about 1 to about 30 carbon atoms. Representative but non-exhaustive examples of alcohols which can be alkoxylated according to the present invention are: 1-dodecanol; 1-tridecanol; 1-tetradecanol; 1-pentadecanol; 1-hexadecanol; 1-heptadecanol; 1-octadecanol; 1-nonadecanol; 1-eicosanol; 1-docosanol; 2-methyl-1-undecanol; 2-propyl-1-nonanol; 2-butyl- 1-octanol; 2-methyl-1-tridecanol; 2-ethyl-i -dodecanol; 2-propyl-1-undecanol; 2-butyl- 1-decanol; 2-pentyl- 1-nonanol, 2-hexyl- 1-octanol; 2-methyl-1-pentadecanol, 2-ethyl-1-tetradecanol; 2-propyl- 1-tridecanol; 2-butyl-1-dodecanol; 2-pentyl- 1-undecanol; 2-hexyl-1-decanol; 2-heptyl- 1-decanol; 2-hexyl- 1-nonanol; 2-octyl- 1-octanol; 2-methyl-1-heptadecanol; 2-ethyl-1-hexadecanol; 2-propyl- 1-pentadecanol; 2-butyl-1-tetradecanol; 1-pentyl- 1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetradecanol; 3-tetradecanol; 4-tetradecanol; 5-tetradecanol; 6-tetradecanol; 7-tetradecanol; 2-hexadecanol; 3-hexadecanol, 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol, 7-octadecanol; 8-octadecanol; 9-octadecanol; 9-octadecenol; 2,4,6-trimethyl-1-heptanol; 2,4,6,8-tetramethyl- 1-nonanol; 3,5,5-trimethyl- 1-hexanol; 3,5,5,7,7-pentamethyl-1-octanol; 3-butyl- 1-nonanol; 3-butyl- 1-undecanol; 3-hexyl- 1-undecanol; 3-hexyl- 1-tridecanol; 3-octyl-1-tridecanol 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol; tetracosanol; hexacosanol; octacosanol; triacontanol; dotriacontanol; hexatriacontanol; 2-decyltetradecanol; 2-dodecylhexadecanol; 2-tetradecyloctadecanol; 2-hexadecyleicosanol, and unsaturated alcohols such as 1-hexyn-3-ol; oleyl alcohol (technically cis-9-octadecene 1-ol); 2,5-dimethyl-4-octyne-3,6-diol 2,4,7, 9-tetramethyl-n-decyne-4,7-diol;, 3-dodecene-1-ol; and 3,6- dimethyl-8-dodecene- 1-ol.

While the invention is effective to alkoxylate all classes of alcohols, including but not necessarily limited to saturated and unsaturated alcohols, saturated alcohols are preferred. Of these, polyalkylene glycols are preferred, with polyethylene glycol being most preferred.

The alkoxylation reaction may be catalyzed using any suitable catalyst. Both basic and acidic catalysts may be used. Suitable catalysts include, but are not neesaily limited to: potassium hydroxide sodium hydroxide; alkylated aluminum fluorides, alkylated aluminum halides organoaluminum zinc compounds, calcium, strontium and barium acetates and naphthanatesI $BF_3$ or $SiF_4$ and metal alkyls or metal alkoxides; and, hydrotluoric acids and metal alkoxides.

The alkoxylation may be carried out at ambient pressure or at pressures above or below ambient, as long as the alkylene oxide is maintained in the vapor phase. Normally, the pressure is from about −14 to about 30 pounds per square inch (psi). Pressures below about 20 psi are preferred. Referring to FIG. 1, in order to conduct the reaction, a suitable reactor that can hold vacuum and pressure may be modified to receive gas or vapor into the top of the reactor. The top of the stainless steel receptacle 16 containing liquid and gaseous ethylene oxide is connected with a tube, hose, or pipe 12 to the vent hole 14 on the reactor head 15. The flow of ethylene oxide gas or vapor is controlled by the valves on the tube 12. The tube 12 preferably includes a "tee" with two valves 18 so that the existing vent hole 14 on the reactor head 15 can be used both for charging ethylene oxide vapor into the reactor 10 through the tube 12 and for venting the reactor 10. A more preferred alternative is to use a reactor with a separate vent hole for venting reactor pressure. Ethylene oxide vapors are allowed to diffuse from the receptacle 16 into the reactor 10 through the tube 12. The separate vent hole is used to release residual inert atmosphere in the reactor once all of the charged ethylene oxide has reacted.

Suitable alkylene oxide adducting materials are alpha and beta alkylene oxides, preferably ethylene oxide, propylene oxide or mixtures thereof most preferably ethylene oxide. The alkoxylated product may have any desired content of the alkoxy adducting material. Where an alcohol is ethoxylated, ethylene oxide will normally comprise from about 20 to about 90 wt% of the alkoxylated product.

A suitable amount of catalyst for use in the reaction is from about 0.05 to about 10.0 weight percent catalyst based upon the weight of the total reaction mixture. Preferred levels of catalyst are from about 0.1 to about 6.0 wt% based on the total reaction mixture weight.

The invention will be better understood with reference to the following examples, which are provided to illustrate the invention, but not to limit the invention.

EXAMPLE 1

After observing undesirable flock in batches of ethoxylated heavy ethylene glycol (EHEG), a series of experiments was performed to determine the cause for flocculation. No correlation could be observed between the percentage of flock and: the percentage of catalyst (in this case, KOH); the reaction temperature (100–160° C.); the oxide addition rate; or the hydroxyl number.

EXAMPLE 2

Experiments were undertaken to determine whether ethoxylation using only ethylene oxide vapors would prevent flock formation. In the following reaction, ethylene oxide vapor was allowed to diffuse through a tube into a Parr reactor and into contact with the substrate—flash heavy ethylene glycol (FHEG, a stream of PEG produced by Oxychem from which light ends were stripped out). The following

| Rxn. # | FHEG (g) | KOH | EO added | Total EO | Total Product | Sample (g) | % $H_2O$ | Base #[1] | Th Base #[1] | ° F.[2] | hr. |
|---|---|---|---|---|---|---|---|---|---|---|---|
| 1319-147 (liq. EO) | 957.03 | | | | 957.03 | a. 110.12 | .03 | | | 230 | |
| | 846.91 | 5 (aq) | | | 851.91 | | | | | 320 | |
| | 846.91 | 1.528 | | | 848.4- | b. 64.39 | 0.11 | 2.08 | 2.65 | 320 | 0.7 |
| | 782.64 | 1.41 | 250 | 250 | 1034 | c. 204.1 | | | 2.01 | 320 | 0.4 |
| | 628.2 | 1.13 | | 200.7 | 829.95 | d. 800.01 | | | | | |
| 1319-149 (liq. EO) | 1029.2 | | | | 1029.2 | | | | | | |
| | 1029.2 | 0.6 | | | 1029.8 | | | | 0.262 | | |
| | 1029.2 | 0.183 | | | 1029.4 | a. 116.9 | | | 0.262 | 320 | 0.08 |
| | 912.32 | 0.163 | 20 | | 932.48 | | | | 0.257 | 320 | 0.75 |
| 1319-151 (EO gas or vap.) | 1028.1 | | | | | | | | | 82 | |
| | 1028.1 | 3 | | | 1031.1 | | | | 1.31 | | |
| | 1028.1 | 0.917 | | | 1029 | a. 33.93 | 0.102 | 0.969 | 1.312 | 223 | 2.75 |
| | 994.2 | 0.887 | | | 995.1 | b. 62.91 | 0.06 | 0.985 | 1.312 | 225 | 1.08 |
| | 931.35 | 0.831 | 20 | 20 | 952.18 | | | | 1.28 | 267 | 1.08 |
| | 931.35 | 0.831 | 90 | 110 | 1042.2 | | | | 1.17 | 270 | 6.8 |
| | 931.35 | 0.831 | 185 | 295 | 1227.2 | c. 12.0 | | | 0.997 | 270 | 8? |

[1]In equivalency in terms of mg of KOH per g of sample.
[2]Reactor temperature.

The last listed sample 1319-151 exhibited an OH# of 435.6. The samples from reaction 1319-151 remained clear without any trace of flock throughout an observation period of several months. Both 1319-147 and 1319-149 were synthesized with liquid ethylene oxide, and both developed flock.

EXAMPLE 3

To demonstrate that using liquid ethylene oxide for ethoxylation would promote flock formation, a clear sample of PEG 200 (from a commercial vendor, similar to FHEG) was ethoxylated with liquid ethylene oxide under the following conditions:

| PEG 200 (g) | KOH | EO added | Total EO | Total Product | Sample (g) | % H$_2$O | OH # | Base #[1] | Th Base #[1] | °F.[2] | hr |
|---|---|---|---|---|---|---|---|---|---|---|---|
| 848.3 | 2.5 | | | | | | | | | | |
| | 0.764 | | | | A. 30.13 | 0.026 | 574.4 | 1.12 | 1.33 | 230 | 23 |
| 818.2 | 0.74 | 200 | 200 | 1018.9 | B. 172.1 | | 439.9 | 0.74 | 1.07 | 230 | 1 |
| 680 | 0.61 | | 166.22 | 846.9 | C. 96.73 | | | | | 230 | |
| 602.3 | 0.54 | | 147.23 | 750.1 | D. 713 | | | | | | |

[1]In equivalency in terms of mg of KOH per g of sample
[2]Reactor temperature.

All samples developed flock within 24 hours.

EXAMPLE 4

In order to confirm the results in Example 2, another reaction was conducted. The ethylene oxide vapors were added through the dip tube (20 in FIG. 1). The reaction is summarized below:

| Rxn. # | FHEG | KOH | EO | Total | Sample | % H$_2$O | Base # | °F. | hr. | Appearance |
|---|---|---|---|---|---|---|---|---|---|---|
| 1319-159 (EO vap.) | 1001.9 (aq) | 2.92 | | | | | | | | |
| | 1001.9 | 0.89 | | 1002.8 | a. 39.95 | 0.3 | 1.87 | 230 | 1.1 | clear |
| | 961.99 | 0.857 | | 962.8 | b. 31.8 | 0.07 | 0.87 | 230 | 1.25 | clear |
| | 930.2 | 0.829 | 286 | 1217 | c. 55.04 | | 0.78 | 260 | | clear |
| | 887.53 | 0.791 | 272.9 | 1161.2 | d. 1121.5 | | | | | clear |

The OH# of the sample with 930.2 FHEG was 448.7.

Samples and products from all previous reactions in which ethylene oxide liquid was charged to the reactor developed flock in less than 24–48 hours. In contrast, all of the samples from reaction 1319-159 were sparkling clear with no flock after 5 days at ambient temperature, and remained clear throughout an observation period of several months.

EXAMPLE 5

Seven more ethoxylations were conducted in Parr reactors using ethylene oxide in the vapor phase. The conditions and results are given in the following Table:

| FHEG | KOH | EO add. | Total EO | Total | Sample | % H$_2$O | BASE # | OH # | °F. | hr. | Appearance |
|---|---|---|---|---|---|---|---|---|---|---|---|
| Reaction 1319-163 (EO vapors to vapor space with about 30" of vacuum initially) | | | | | | | | | | | |
| 995.1 | 2.95 | | | | | | | | | | |
| 995.1 | 0.902 | | | 996 | A. 58.78 | 0.09 | 0.9 | | 230 | | clear |
| 936.4 | 0.85 | | | 937.22 | B. 41.25 | 0.05 | 0.9 | | 230 | 0.5 | clear |
| 895.2 | 0.81 | 260 | 260 | 1156 | C. 74.67 | | | | 260 | 2.5 | sl. hazy |
| 837.34 | 0.76 | | 243.2 | 1081.3 | D. 1034.8 | | | | | | sl. hazy |
| Reaction 1319-165 (EO vapor to vapor space with about 30" of vacuum initially) | | | | | | | | | | | |
| 990.4 | 2.85 | | | | | | | | | | |
| 990.4 | 0.87 | | | 991.27 | A. 39.9 | | | | 230 | 1.75 | clear |
| 950.5 | 0.84 | | | 951.4 | B. 35.12 | | | | | | clear |
| 915.5 | 0.805 | 275 | 275 | 1191.3 | C. 55.93 | | | | 266 | 2.7 | clear |
| 872.5 | 0.767 | | 262.09 | 1135.3 | D. 1009 | | 0.63 | 443.8 | | | clear |
| 1319-167 (EO vapor to vapor phase with about 30" vacuum initially) | | | | | | | | | | | |
| 995.8 | 2.95 | | | | | | | | | | |
| 995.8 | 0.902 | | | 996.7 | A. 25.56 | 0.05 | 0.8 | | 230 | 1.25 | clear |
| 970.26 | 0.878 | | | 971.14 | B. 32.3 | 0.02 | 0.81 | | 230 | | clear |
| 937.99 | 0.849 | 291 | 291 | 1229.8 | C. 52.51 | | | | 230 | 3.38 | sl.hazy |
| 897.9 | 0.81 | | 278.6 | 1177.3 | D. 1107 | | 0.65 | 437.1 | | | sl. hazy |

-continued

| FHEG | KOH | EO add. | Total EO | Total | Sample | % H$_2$O | BASE # | OH # | °F. | hr. | Appearance |
|---|---|---|---|---|---|---|---|---|---|---|---|
| 1319-169 (EO vapor through dip tube with about 30" of vacuum initially--the EO cylinder was very full) | | | | | | | | | | | |
| 940.3 | 2.87 | | | | | | | | | | |
| 940.3 | 0.877 | | | | A. 32.33 | 0.1 | | | 230 | 1 | clear |
| 907.98 | 0.847 | | | 908.8 | B. 32.56 | 0.05 | 0.89 | | 230 | 1 | clear |
| 875.45 | 0.817 | 115 | 115 | 991.3 | C. 64.46 | | 0.79 | 522.1 | 230 | 1 | clear |
| 818.08 | 0.763 | 125 | 232.5 | 1051.3 | D. 64.3 | | 0.75 | 456.1 | 230 | 0.75 | clear |
| 768.04 | 0.717 | | 218.3 | 987.01 | E. 233.5 | | | | | | clear |
| 586.35 | 0.547 | 50 | 216.61 | 803.5 | F. 740.3 | | | | | | clear |
| Reaction 1319-171 (EO vapors via diptube with about 30" of vacuum initially) | | | | | | | | | | | |
| 783.3 | 2.4 | | | 785.7 | | | | | | | |
| | 0.73 | | | 784.03 | a. 44 | 0.12 | 0.9 | | 230 | 1.1 | |
| | | | | | b. 63.2 | 0.06 | 0.9 | | 230 | 0.4 | — purge and vac. 30" |
| 676.2 | 0.63 | 200 | 200 | 876.8 | c. 107.4 | | | | 230 | 2.25 | ? |
| 593.4 | 0.556 | | 175.5 | 769.4 | d. 727.4 | | | 451.5 | | | sl. flock |
| 1319-173 (EO vapors through diptube with about 30" of vacuum initially) | | | | | | | | | | | |
| 805.1 | 2.5 | | | 807.6 | | | | | | | |
| 805.1 | 0.76 | | | 803.86 | a. 27.7 | 0.15 | 1 | | 230 | 1 | |
| | | | | | b. 16.2 | 0.07 | 0.95 | | 230 | 1.25 | N$_2$ purge vac. 30" |
| 761.24 | 0.722 | 228 | 228 | 989.96 | c. 110 | | | | 230 | 1.25 | EO in continuously |
| 676.7 | 0.64 | 202.7 | 202.7 | 879.96 | d. 830.1 | | | | | | clear |
| 1319-175 (EO vapors to vapor space with vacuum) | | | | | | | | | | | |
| 767.9 | 2.38 | | | 770.3 | | | | | | | |
| 767.9 | 0.73 | | | 768.6 | a. 16.83 | 0.18 | 0.96 | | 230 | 1 | |
| 751.1 | 0.71 | | | 751.8 | b. 18.1 | 0.08 | 0.96 | | 230 | 1 | N$_2$ purge vac. 30" |
| 732.99 | 0.694 | 220 | 220 | 953.7 | c. 106.2 | | | | | | EO in intermittently |
| 651.37 | 0.617 | | 195.5 | 847.49 | d. | | | | | | clear |

The samples from 1319-163, -165, -167, -169, -173, and -175 largely remained clear throughout an observation period of several months. A number of the samples developed a slight flock later and appeared slightly hazy. The amounts of flock in these samples were less than those present in samples synthesized with liquid EO. Also, the flock was finer and was more evenly distributed. It was believed that if the EO vapor is pulled from the EO container too fast, rapid effervescence or flash boiling of EO liquid would cause fine liquid droplets of EO to be carried into the reactor, thereby incorporating liquid EO in the reactions.

EXAMPLE 6

An experiment (1319-177) was performed using an atomizer to discharge EO vapors into the Parr reactor. The atomizer was installed onto the diptube of one of the Parr reactors in which the length of the dip tube was shortened by cutting off about two inches. In another experiment using a different reactor (1319-179), EO vapors were charged into the reactor vapor phase with an initial vacuum pressure of about 5" mercury. The conditions and results are summarized in the following Table:

| FHEG | KOH | EO added | Total EO | Total | Sample | % H$_2$O | Base # | OH # | °F. | hr. | Appearance |
|---|---|---|---|---|---|---|---|---|---|---|---|
| \multicolumn{12}{c}{Reaction 1319-177 (EO vapor through diptube and atomizer, 30" var.)} |
| 1334 | 4.13 | | | 1338.1 | | | | | | | |
| 1334 | 1.26 | | | 1335.3 | a. 32.33 | 0.4 | 0.92 | | 230 | 2.1 | Drying without nitrogen sparge |
| 1301.7 | 1.23 | | | 1302.9 | b. 76.3 | 0.1 | 0.95 | | 230 | 1.3 | |
| 1225.5 | 1.16 | 255 | | 1481.6 | | | | | 230 | 3.611 | |
| 1225.1 | 1.16 | 100 | 355 | 1581.6 | | | | | 230 | 1.6 | |
| 1225.1 | 1.16 | | 355 | 1581.6 | c. 1540.1 | | | 453.3 | | | clear (4 days) |
| \multicolumn{12}{c}{Reaction 1319-179 (EO vapors to vapor phase w/5" vacuum pressue initially)} |
| 831.7 | 2.43 | | | 834.13 | | | | | | | |
| 831.7 | 0.743 | | | 832.44 | a. 44.3 | 0.11 | 0.94 | | 230 | 1.1 | |
| 787.4 | 0.703 | | | 788.14 | b. 45.3 | 0.01 | 0.92 | | 230 | 1 | |
| 742.18 | 0.663 | 134 | 134 | 874.84 | | | | | 230 | 1.2 | |
| 742.18 | 0.663 | 88 | 220 | 962.84 | | | | | 230 | 1.2 | |
| 742.18 | 0.663 | | 220 | 962.84 | c. 926.7 | | | 444.7 | | | clear (4 days) |

The products were clear initially and remained clear throughout an observation period of several months.

EXAMPLE 7

In reaction 1319-183, liquid EO was added or charged into the reactor containing FHEG via the same atomizer used for reaction 1319-177. The resulting product had flock.

EXAMPLE 8

The procedures of Example 2 were repeated. No vacuum was used. The conditions and results are summarized in the following Table:

The samples were clear and remained clear throughout an observation period of several months.

EXAMPLE 9

A mixture of PEG 200 and KOH flakes was charged into a Parr reactor and dried. The procedures of Example 2 then were repeated. The conditions and results are summarized in the following Table:

| FHEG | KOH | EO added | Total EO | Total | Sample | % H$_2$O | Base # | °F. | hr. | Appearance |
|---|---|---|---|---|---|---|---|---|---|---|
| 551.5 | 1.61 | | | 553.11 | | | | 220 | | |
| 551.5 | 0.49 | | | 551.99 | a. 24.18 | 0.095 | 10.6 | 215 | 2.3 | |
| 527.34 | 0.47 | 48 | 48 | 575.81 | | | | 265 | 2.1 | |
| 527.34 | 0.47 | 89 | 137 | 664.81 | | | | 265 | 6 | |
| 527.34 | 0.47 | 30 | 167 | 194.81 | | | | 260 | 2.5 | |
| 527.34 | 0.47 | | 167 | 694.81 | b. 38.2 | | | 260 | 2.5 | clear |

| PEG 200 | KOH | EO added | Total EO | Total | Sample | % H₂O | Base # | ° F. | hr. | Appearance |
|---|---|---|---|---|---|---|---|---|---|---|
| Reaction 1318-155 (EO vapor to reactor head space) ||||||||||| 
| 803.54 | 2.34 | | | | | | | | | |
| 803.54 | 0.715 | | | | a. 31.2 | 0.22 | | 230 | 1.6 | |
| | | | | | b. 8.7 | 0.14 | | 230 | 2.5 | |
| | | | | | c. 12.3 | 0.19 | | 230 | 1.2 | |
| | | | | | d. 16 | 0.16 | | 240 | 1.6 | |
| 735.4 | 0.654 | | | 736.06 | e. 16.8 | 0.23 | | 240 | 1.6 | |
| 718.6 | 0.64 | 122 | 122 | 841.3 | f. 238.9 | | | 230 | 2.5 | clear |
| 514.5 | 0.46 | 38 | 125.4 | 640.6 | g. 202.1 | | | 230 | 1.6 | clear |
| 352.2 | 0.31 | 32 | 117.8 | 470.3 | h. 204.4 | | | 230 | 1.7 | clear |
| 199.1 | 0.18 | 20 | 86.6 | 285.9 | i. 283 | | | 230 | 1.95 | clear |

The samples were clear and remained clear throughout an observation period of several months.

EXAMPLE 10

The procedures of Example 9 were repeated using an initial vacuum of 10" inside the reactor. The reaction (1318-157) and results are summarized in the following Table:

| PEG 200 | KOH | EO added | Total EO | Total | Sample | % H₂O | ° F. | hr. |
|---|---|---|---|---|---|---|---|---|
| 835.33 | 2.43 | | | 837.76 | | | | |
| 835.33 | 0.743 | | | 836.07 | a. 14.7 | 0.06 | 230 | 5.3 |
| 820.64 | 0.73 | | | 821.37 | | | | |
| 820.64 | 0.73 | 128 | 128 | 949.37 | | | 230 | 2.2 |
| 820.64 | 0.73 | 132 | 260 | 1081.4 | b. 1018.6 | | 230 | 4.3 |

The samples were clear and remained clear throughout an observation period of several months.

EXAMPLE 11

Finally, an ethoxylation with EO vapor was conducted in a 60-gallon reactor in the pilot plant. The reaction (1318-159) is summarized below:

| FHEG | KOH (g) | EO added | Total EO | Sample | % H₂O | Base # | ° F. | hr. | Appearance |
|---|---|---|---|---|---|---|---|---|---|
| 248 lb | 148 | | | a. 6 oz | 0.38 | | 220 | 5 | clear |
| | | | | b. 16 oz | 0.08 | 5927 | 220 | 7 | clear |
| | | 78 lb. | 78 lb. | c. 16 oz | | 4685 | | | clear |
| | | 13 lb. | 19 lb. | d. 336 lb. | | 433 | | | clear |

All samples remained clear for at least one month.

Persons of ordinary skill in the art will appreciate that many modifications may be made to the embodiments described herein without departing from the spirit of the present invention. Accordingly, the embodiments described herein are illustrative only and are not intended to limit the scope of the present invention.

I claim:

1. A method of reducing flock during alkoxylation comprising:

providing a feed receptacle comprising alkylene oxide comprising a liquid fraction and a vapor fraction;

diffusing said alkylene oxide consisting essentially of at least a portion of said vapor fraction from said feed receptacle to a reaction vessel; and reacting an organic compound adapted to be alkoxylated with said portion of said vapor fraction, producing an alkoxylation product;

wherein said alkoxylation product comprises a reduced amount of flock compared to a quantity of flock produced when said liquid fraction is withdrawn from said feed receptacle and reacted with said organic compound.

2. The method of claim 1 wherein said diffusing comprises applying a vacuum to withdraw said at least a portion of said vapor fraction from said feed receptacle.

3. The method of claim 1 wherein said organic compound is an alcohol.

4. The method of claim 2 wherein said organic compound is an alcohol.

5. The method of claim 1 wherein said organic compound is a polyhydric alcohol.

6. The method of claim 2 wherein said organic compound is a polyhydric alcohol.

7. The method of claim 1 wherein said organic compound is selected from the group consisting of aldehydes, ketones, amides, amines, organic acids, phenols and alkyl phenols, polyols, mercaptans, alcohols, and saturated, unsaturated, linear, and branched polyhydric alcohols.

8. The method of claim 2 wherein said organic compound is selected from the group consisting of aldehydes, ketones, amides, amines, organic acids, phenols and alkyl phenols, polyols, mercaptans, alcohols, and saturated, unsaturated, linear, and branched polyhydric alcohols.

9. The method of claim 1 wherein said organic compound is selected from the group consisting of polyhydric alcohols containing a total of from about 2 to about 30 carbon atoms and having the general formula

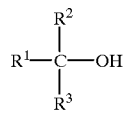

wherein $R^1$, $R^2$, and $R^3$ independently are selected from the group consisting of linear or branched acyclic groups, alicyclic groups, aryl groups, cyclic groups, and hydrogen and may contain one or more functional groups selected from the group consisting of amine, carboxyl, hydroxy, halogen, nitro, carbonyl, and amide;

aldehydes and ketones, having from about 2 to about 30 carbon atoms and having the general formula

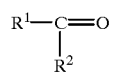

wherein $R^1$ and $R^2$ independently are selected from the group consisting of hydrogen, linear or branched acyclic groups, alicyclic groups, cyclic groups, and aryl groups, and may contain one or more functionalities selected from the group consisting of carboxyl groups, hydroxyl groups, halogen atoms, nitro-groups, amine groups, and amide groups;

primary, secondary or tertiary amides, having from about 1 to about 30 carbon atoms and having the general formula

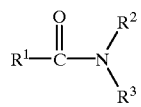

wherein $R^1$, $R^2$, and $R^3$ independently are selected from the group consisting of hydrogen, linear or branched acyclic groups, alicyclic groups, cyclic groups, aryl groups, and may contain one or more functionalities selected from the group consisting of hydroxyl groups, carboxyl groups, carbonyl groups, amine groups, nitro-groups, or halogen atoms;

primary, secondary, or tertiary amines, having from about 1 to about 30 carbon atoms, and having the general formula

wherein $R^1$, $R^2$, and $R^3$ independently are selected from the group consisting of hydrogen, linear or branched acyclic groups, alicyclic groups, cyclic groups, or aryl groups, and may contain one or more functionalities selected from the group consisting of a hydroxyl group, a carbonyl group, a halogen atom, a carboxyl group, a nitro-group, or an amide group;

organic acids, having from about 1 to about 30 carbon atoms, and having the general formula

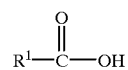

wherein $R^1$ is a hydrogen, a linear or branched acyclic group, alicyclic group, cyclic group, or aryl group, and may contain one or more functionalities selected from the group consisting of a carbonyl group, a hydroxyl group, a halogen atom, a nitro-group, an amine group, or an amide group;

alkyl phenols, having from about 6 to about 30 carbon atoms and having the general formula

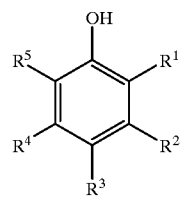

wherein $R^1$, $R^2$, $R^3$, $R^4$, and $R^5$ independently are selected from the group consisting of hydrogen, a halogen atom, a hydroxyl group, a nitro-group, a carbonyl group, a linear or branched acyclic group, an alicyclic group, a cyclic group, an aryl group, or a substituted aryl group, and may contain one or more functionalities selected from the group consisting of a halogen atom, an ether group, a nitro-group, a carboxyl group, a carbonyl group, an amine group, an amide group, or a hydroxyl group;

mercaptans of the general formula

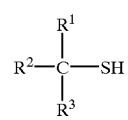

wherein $R^1$, $R^2$ and $R^3$ independently are selected from the group consisting of hydrogen, linear or branched acyclic groups, alicyclic groups, cyclic groups, and aryl groups having from about 1 to about 30 carbon atoms, and may contain one or more functionalities selected from the group consisting of carboxyl groups, hydroxyl groups, a halogen atom, a nitro-group, an amine group, or an amide group; and alcohols having the general formula ROH wherein R is selected from the group consisting of a linear or branched alkyl group having from about 1 to about 30 carbon atoms, an aryl group, a cyclic group having from about 6 to about 30 carbon atoms, and olefinic and acetylenic groups having from about 1 to about 30 carbon atoms.

10. The method of claim 2 wherein said organic compound is selected from the group consisting of polyhydric alcohols containing a total of from about 2 to about 30 carbon atoms and having the general formula

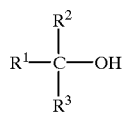

wherein $R^1$, $R^2$, and $R^3$ independently are selected from the group consisting of linear or branched acyclic groups, alicyclic groups, aryl groups, cyclic groups, and hydrogen and may contain one or more functional groups selected from the group consisting of amine, carboxyl, hydroxy, halogen, nitro, carbonyl, and amide;

aldehydes and ketones, having from about 2 to about 30 carbon atoms and having the general formula

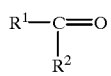

wherein $R^1$ and $R^2$ independently are selected from the group consisting of hydrogen, linear or branched acyclic groups, alicyclic groups, cyclic groups, and aryl groups, and may contain one or more functionalities selected from the group consisting of carboxyl groups, hydroxyl groups, halogen atoms, nitro-groups, amine groups, and amide groups;

primary, secondary or tertiary amides, having from about 1 to about 30 carbon atoms and having the general formula

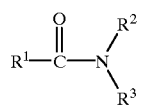

wherein $R^1$, $R^2$, and $R^3$ independently are selected from the group consisting of hydrogen, linear or branched acyclic groups, alicyclic groups, cyclic groups, aryl groups, and may contain one or more functionalities selected from the group consisting of hydroxyl groups, carboxyl groups, carbonyl groups, amine groups, nitro-groups, or halogen atoms;

primary, secondary, or tertiary amines, having from about 1 to about 30 carbon atoms, and having the general formula

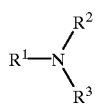

wherein $R^1$, $R^2$, and $R^3$ independently are selected from the group consisting of hydrogen, linear or branched acyclic groups, alicyclic groups, cyclic groups, or aryl groups, and may contain one or more functionalities selected from the group consisting of a hydroxyl group, a carbonyl group, a halogen atom, a carboxyl group, a nitro-group, or an amide group;

organic acids, having from about 1 to about 30 carbon atoms, and having the general formula

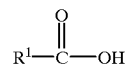

wherein $R^1$ is a hydrogen, a linear or branched acyclic group, alicyclic group, cyclic group, or aryl group, and may contain one or more functionalities selected from the group consisting of a carbonyl group, a hydroxyl group, a halogen atom, a nitro-group, an amine group, or an amide group;

alkyl phenols, having from about 6 to about 30 carbon atoms and having the general formula

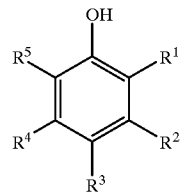

wherein $R^1$, $R^2$, $R^3$, $R^4$, and $R^5$ independently are selected from the group consisting of hydrogen, a halogen atom, a hydroxyl group, a nitro-group, a carbonyl group, a linear or branched acyclic group, an alicyclic group, a cyclic group, an aryl group, or a substituted aryl group, and may contain one or more functionalities selected from the group consisting of a halogen atom, an ether group, a nitro-group, a carboxyl group, a carbonyl group, an amine group, an amide group, or a hydroxyl group;

mercaptans of the general formula

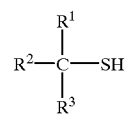

wherein $R^1$, $R^2$ and $R^3$ independently are selected from the group consisting of hydrogen, linear or branched acyclic groups, alicyclic groups, cyclic groups, and aryl groups having from about 1 to about 30 carbon atoms, and may contain one or more functionalities selected from the group consisting of carboxyl groups, hydroxyl groups, a halogen atom, a nitro-group, an amine group, or an amide group; and alcohols having the general formula ROH wherein R is selected from the group consisting of a linear or branched alkyl group having from about 1 to about 30 carbon atoms, an aryl group, a cyclic group having from about 6 to about 30 carbon atoms, and olefinic and acetylenic groups having from about 1 to about 30 carbon atoms.

11. A method of reducing flock during alkoxylation comprising:
providing a feed receptacle comprising alkylene oxide comprising a liquid fraction and a vapor fraction;
diffusing said alkylene oxide consisting essentially of at least a portion of said vapor fraction from said feed receptacle to said reaction vessel; and
reacting a polyalkylene glycol with said portion of said vapor fraction, producing an alkoxylation product;
wherein said alkoxylation product comprises a reduced amount of flock compared to a quantity of flock produced when said liquid fraction is withdrawn from said feed receptacle and reacted with said organic compound.

12. The method of claim 11 wherein said diffusing comprises applying a vacuum to withdraw said at least a portion of said vapor fraction from said feed receptacle.

13. The method of claim 1 wherein said organic compound is selected from the group consisting of polyethylene glycol and polypropylene glycol.

14. The method of claim 2 wherein said organic compound is selected from the group consisting of polyethylene glycol and polypropylene glycol.

15. The method of claim 1 wherein said organic compound is polyethylene glycol.

16. The method of claim 2 wherein said organic compound is polyethylene glycol.

17. A method of reducing flock during alkoxylation comprising:
    providing a feed receptacle comprising an alkylene oxide comprising a liquid fraction and a vapor fraction, said alkylene oxide being selected from the group consisting of ethylene oxide and propylene oxide;
    diffusing said alkylene oxide consisting essentially of at least a portion of said vapor fraction from said feed receptacle to said reaction vessel; and
    reacting an organic compound adapted to be alkoxylated with said portion of said vapor fraction, producing an alkoxylation product;
    wherein said alkoxylation product comprises a reduced amount of flock compared to a quantity of flock produced when said liquid fraction is withdrawn from said feed receptacle and reacted with said organic compound.

18. The method of claim 17 wherein said diffusing comprises applying a vacuum to withdraw said at least a portion of said vapor fraction from said feed receptacle.

19. The method of claim 1 wherein said alkylene oxide is selected from the group consisting of ethylene oxide and propylene oxide.

20. The method of claim 2 wherein said alkylene oxide is selected from the group consisting of ethylene oxide and propylene oxide.

21. The method of claim 3 wherein said alkylene oxide is selected from the group consisting of ethylene oxide and propylene oxide.

22. The method of claim 4 wherein said alkylene oxide is selected from the group consisting of ethylene oxide and propylene oxide.

23. The method of claim 5 wherein said alkylene oxide is selected from the group consisting of ethylene oxide and propylene oxide.

24. The method of claim 6 wherein said alkylene oxide is selected from the group consisting of ethylene oxide and propylene oxide.

25. The method of claim 7 wherein said alkylene oxide is selected from the group consisting of ethylene oxide and propylene oxide.

26. The method of claim 8 wherein said alkylene oxide is selected from the group consisting of ethylene oxide and propylene oxide.

27. The method of claim 9 wherein said alkylene oxide is selected from the group consisting of ethylene oxide and propylene oxide.

28. The method of claim 10 wherein said alkylene oxide is selected from the group consisting of ethylene oxide and propylene oxide.

29. The method of claim 11 wherein said alkylene oxide is selected from the group consisting of ethylene oxide and propylene oxide.

30. The method of claim 12 wherein said alkylene oxide is selected from the group consisting of ethylene oxide and propylene oxide.

31. The method of claim 13 wherein said alkylene oxide is selected from the group consisting of ethylene oxide and propylene oxide.

32. The method of claim 14 wherein said alkylene oxide is selected from the group consisting of ethylene oxide and propylene oxide.

33. The method of claim 15 wherein said alkylene oxide is selected from the group consisting of ethylene oxide and propylene oxide.

34. The method of claim 16 wherein said alkylene oxide is selected from the group consisting of ethylene oxide and propylene oxide.

35. The method of claim 1 wherein said alkylene oxide is ethylene oxide.

36. The method of claim 2 wherein said alkylene oxide is ethylene oxide.

37. The method of claim 3 wherein said alkylene oxide is ethylene oxide.

38. The method of claim 4 wherein said alkylene oxide is ethylene oxide.

39. The method of claim 5 wherein said alkylene oxide is ethylene oxide.

40. The method of claim 6 wherein said alkylene oxide is ethylene oxide.

41. The method of claim 7 wherein said alkylene oxide is ethylene oxide.

42. The method of claim 8 wherein said alkylene oxide is ethylene oxide.

43. The method of claim 9 wherein said alkylene oxide is ethylene oxide.

44. The method of claim 10 wherein said alkylene oxide is ethylene oxide.

45. The method of claim 11 wherein said alkylene oxide is ethylene oxide.

46. The method of claim 12 wherein said alkylene oxide is ethylene oxide.

47. The method of claim 13 wherein said alkylene oxide is ethylene oxide.

48. The method of claim 14 wherein said alkylene oxide is ethylene oxide.

49. The method of claim 15 wherein said alkylene oxide is ethylene oxide.

50. The method of claim 16 wherein said alkylene oxide is ethylene oxide.

51. A method of reducing flock during alkoxylation comprising:
    providing a feed receptacle comprising alkylene oxide comprising a liquid fraction and a vapor fraction;
    diffusing said alkylene oxide consisting of at least a portion of said vapor fraction from said feed receptacle to a reaction vessel; and
    reacting an organic compound adapted to be alkoxylated with said portion of said vapor fraction, producing an alkoxylation product;
    wherein said alkoxylation product comprises a reduced amount of flock compared to a quantity of flock produced when said liquid fraction is withdrawn from said feed receptacle and reacted with said organic compound.

52. The method of claim 51 wherein said diffusing comprises applying a vacuum to withdraw said at least a portion of said vapor fraction from said feed receptacle.

53. The method of claim 51 wherein said organic compound is an alcohol.

54. The method of claim 52 wherein said organic compound is an alcohol.

55. The method of claim 51 wherein said organic compound is a polyhydric alcohol.

56. The method of claim 52 wherein said organic compound is a polyhydric alcohol.

57. The method of claim 51 wherein said organic compound is selected from the group consisting of aldehydes, ketones, amides, amines, organic acids, phenols and alkyl phenols, polyols, mercaptans, alcohols, and saturated, unsaturated, linear, and branched polyhydric alcohols.

58. The method of claim 52 wherein said organic compound is selected from the group consisting of aldehydes, ketones, amides, amines, organic acids, phenols and alkyl phenols, polyols, mercaptans, alcohols, and saturated, unsaturated, linear, and branched polyhydric alcohols.

59. The method of claim 51 wherein said organic compound is selected from the group consisting of polyhydric alcohols containing a total of from about 2 to about 30 carbon atoms and having the general formula

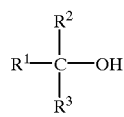

wherein $R^1$, $R^2$, and $R^3$ independently are selected from the group consisting of linear or branched acyclic groups, alicyclic groups, aryl groups, cyclic groups, and hydrogen and may contain one or more functional groups selected from the group consisting of amine, carboxyl, hydroxy, halogen, nitro, carbonyl, and amide;

aldehydes and ketones, having from about 2 to about 30 carbon atoms and having the general formula

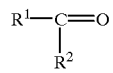

wherein $R^1$ and $R^2$ independently are selected from the group consisting of hydrogen, linear or branched acyclic groups, alicyclic groups, cyclic groups, and aryl groups, and may contain one or more functionalities selected from the group consisting of carboxyl groups, hydroxyl groups, halogen atoms, nitro-groups, amine groups, and amide groups;

primary, secondary or tertiary amides, having from about 1 to about 30 carbon atoms and having the general formula

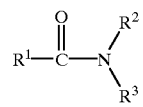

wherein $R^1$, $R^2$, and $R^3$ independently are selected from the group consisting of hydrogen, linear or branched acyclic groups, alicyclic groups, cyclic groups, aryl groups, and may contain one or more functionalities selected from the group consisting of hydroxyl groups, carboxyl groups, carbonyl groups, amine groups, nitro-groups, or halogen atoms;

primary, secondary, or tertiary amines, having from about 1 to about 30 carbon atoms, and having the general formula

wherein $R^1$, $R^2$, and $R^3$ independently are selected from the group consisting of hydrogen, linear or branched acyclic groups, alicyclic groups, cyclic groups, or aryl groups, and may contain one or more functionalities selected from the group consisting of a hydroxyl group, a carbonyl group, a halogen atom, a carboxyl group, a nitro-group, or an amide group;

organic acids, having from about 1 to about 30 carbon atoms, and having the general formula

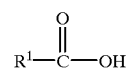

wherein $R^1$ is a hydrogen, a linear or branched acyclic group, alicyclic group, cyclic group, or aryl group, and may contain one or more functionalities selected from the group consisting of a carbonyl group, a hydroxyl group, a halogen atom, a nitro-group, an amine group, or an amide group;

alkyl phenols, having from about 6 to about 30 carbon atoms and having the general formula

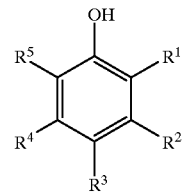

wherein $R^1$, $R^2$, $R^3$, $R^4$, and $R^5$ independently are selected from the group consisting of hydrogen, a halogen atom, a hydroxyl group, a nitro-group, a carbonyl group, a linear or branched acyclic group, an alicyclic group, a cyclic group, an aryl group, or a substituted aryl group, and may contain one or more functionalities selected from the group consisting of a halogen atom, an ether group, a nitro-group, a carboxyl group, a carbonyl group, an amine group, an amide group, or a hydroxyl group;

mercaptans of the general formula

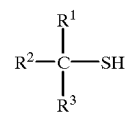

wherein $R^1$, $R^2$ and $R^3$ independently are selected from the group consisting of hydrogen, linear or branched acyclic groups, alicyclic groups, cyclic groups, and aryl groups having from about 1 to about 30 carbon atoms, and may contain one or more functionalities selected from the group consisting of carboxyl groups, hydroxyl groups, a halogen atom, a nitro-group, an amine group, or an amide group; and alcohols having the general formula ROH wherein R is selected from the group consisting of a linear or branched alkyl group having from about 1 to about 30 carbon atoms, an aryl group, a cyclic group having from about 6 to about 30 carbon atoms, and olefinic and acetylenic groups having from about 1 to about 30 carbon atoms.

60. The method of claim wherein 52 said organic compound is selected from the group consisting of polyhydric alcohols containing a total of from about 2 to about 30 carbon atoms and having the general formula

wherein $R^1$, $R^2$, and $R^3$ independently are selected from the group consisting of linear or branched acyclic groups, alicyclic groups, aryl groups, cyclic groups, and hydrogen and may contain one or more functional groups selected from the group consisting of amine, carboxyl, hydroxy, halogen, nitro, carbonyl, and amide;

aldehydes and ketones, having from about 2 to about 30 carbon atoms and having the general formula

wherein $R^1$ and $R^2$ independently are selected from the group consisting of hydrogen, linear or branched acyclic groups, alicyclic groups, cyclic groups, and aryl groups, and may contain one or more functionalities selected from the group consisting of carboxyl groups, hydroxyl groups, halogen atoms, nitro-groups, amine groups, and amide groups;

primary, secondary or tertiary amides, having from about 1 to about 30 carbon atoms and having the general formula

wherein $R^1$, $R^2$, and $R^3$ independently are selected from the group consisting of hydrogen, linear or branched acyclic groups, alicyclic groups, cyclic groups, aryl groups, and may contain one or more functionalities selected from the group consisting of hydroxyl groups, carboxyl groups, carbonyl groups, amine groups, nitro-groups, or halogen atoms;

primary, secondary, or tertiary amines, having from about 1 to about 30 carbon atoms, and having the general formula

wherein $R^1$, $R^2$, and $R^3$ independently are selected from the group consisting of hydrogen, linear or branched acyclic groups, alicyclic groups, cyclic groups, or aryl groups, and may contain one or more flinctionalities selected from the group consisting of a hydroxyl group, a carbonyl group, a halogen atom, a carboxyl group, a nitro-group, or an amide group;

organic acids, having from about 1 to about 30 carbon atoms, and having the general formula

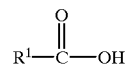

wherein $R^1$ is a hydrogen, a linear or branched acyclic group, alicyclic group, cyclic group, or aryl group, and may contain one or more functionalities selected from the group consisting of a carbonyl group, a hydroxyl group, a halogen atom, a nitro-group, an amine group, or an amide group;

alkyl phenols, having from about 6 to about 30 carbon atoms and having the general formula

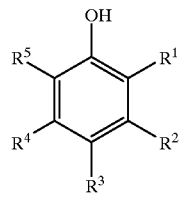

wherein $R^1$, $R^2$, $R^3$, $R^4$, and $R^5$ independently are selected from the group consisting of hydrogen, a halogen atom, a hydroxyl group, a nitro-group, a carbonyl group, a linear or branched acyclic group, an alicyclic group, a cyclic group, an aryl group, or a substituted aryl group, and may contain one or more functionalities selected from the group consisting of a halogen atom, an ether group, a nitro-group, a carboxyl group, a carbonyl group, an amine group, an amide group, or a hydroxyl group;

mercaptans of the general formula

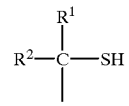

wherein $R^1$, $R^2$ and $R^3$ independently are selected from the group consisting of hydrogen, linear or branched acyclic groups, alicyclic groups, cyclic groups, and aryl groups having from about 1 to about 30 carbon atoms, and may contain one or more functionalities selected from the group consisting of carboxyl groups, hydroxyl groups, a halogen atom, a nitro-group, an amine group, or an amide group; and alcohols having the general formula ROH wherein R is selected from the group consisting of a linear or branched alkyl group having from about 1 to about 30 carbon atoms, an aryl group, a cyclic group having from about 6 to about 30 carbon atoms, and olefinic and acetylenic groups having from about 1 to about 30 carbon atoms.

61. A method of reducing flock during alkoxylation comprising:

providing a feed receptacle comprising an alkylene oxide comprising a liquid fraction and a vapor fraction, said alkylene oxide being selected from the group consisting of ethylene oxide and propylene oxide;

diffusing said alkylene oxide consisting of at least a portion of said vapor fraction from said feed receptacle to said reaction vessel; and reacting an organic compound adapted to be alkoxylated with said portion of said vapor fraction, producing an alkoxylation product;

wherein said alkoxylation product comprises a reduced amount of flock compared to a quantity of flock produced when said liquid fraction is withdrawn from said feed receptacle and reacted with said organic compound.

62. The method of claim 61 wherein said diffusing comprises applying a vacuum to withdraw said at least a portion of said vapor fraction from said feed receptacle.

* * * * *